(12) United States Patent
Green et al.

(10) Patent No.: US 11,328,794 B2
(45) Date of Patent: May 10, 2022

(54) METHOD FOR DETERMINING RELATEDNESS OF GENOMIC SAMPLES USING PARTIAL SEQUENCE INFORMATION

(71) Applicant: The Regents of the University of California, Oakland, CA (US)

(72) Inventors: Richard E. Green, Santa Cruz, CA (US); Samuel H. Vohr, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 716 days.

(21) Appl. No.: 15/319,253

(22) PCT Filed: Jun. 17, 2015

(86) PCT No.: PCT/US2015/036250
§ 371 (c)(1),
(2) Date: Dec. 15, 2016

(87) PCT Pub. No.: WO2015/195816
PCT Pub. Date: Dec. 23, 2015

(65) Prior Publication Data
US 2017/0132360 A1    May 11, 2017

Related U.S. Application Data

(60) Provisional application No. 62/013,734, filed on Jun. 18, 2014.

(51) Int. Cl.
| | |
|---|---|
| *G16B 30/00* | (2019.01) |
| *G16B 20/00* | (2019.01) |
| *G16B 20/40* | (2019.01) |
| *G16B 20/20* | (2019.01) |

(52) U.S. Cl.
CPC ............ *G16B 30/00* (2019.02); *G16B 20/00* (2019.02); *G16B 20/20* (2019.02); *G16B 20/40* (2019.02)

(58) Field of Classification Search
None
See application file for complete search history.

(56) References Cited

U.S. PATENT DOCUMENTS

| | | |
|---|---|---|
| 2002/0077775 A1 | 6/2002 | Schork et al. |
| 2010/0086926 A1 | 4/2010 | Craig et al. |
| 2010/0184040 A1 | 7/2010 | Kirkpatrick et al. |

FOREIGN PATENT DOCUMENTS

WO    2002101626 A1    12/2002

OTHER PUBLICATIONS

Wall et al. Nature Reviews Genetics (2003) vol. 4, pp. 587-597.*
Laan et al. Nature Genetics (1997) vol. 17, pp. 435-438.*
Wang et al. (2009) "Learning your identity and disease from research papers: information leaks in genome wide association study" Proceedings of the 16th ACM conference on Computer and communications security. ACM, 12pgs.
Visscher et al. (2009) "The Limits of Individual Identification from Sample Allele Frequencies: Theory and Statistical Analysis" PLOS Genetics, 5(10):e1000628.
Yang et al. (2006) "A Sliding-Window Weighted Linkage Disequilibrium Test" Genetic Epidemiology, 30(6):531-545.
Li et al. (2009) "SNP detection for massively parallel whole-genome resequencing" Genome Research 19(6):1124-1132 (http://genome.cshlp.org/content/19/6/1124.abstract).
Zhi et al. (2012) "Genotype calling from next-generation sequencing data using haplotype information of reads" Bioinformatics 28(7):938-946.

\* cited by examiner

*Primary Examiner* — Joseph Woitach
(74) *Attorney, Agent, or Firm* — Brian E. Davy; Bozicevic, Field & Francis LLP

(57) ABSTRACT

Disclosed are methods for testing biological samples containing genomic nucleic acids obtained from an organism having a genome, such as a human genome. It is often desirable to analyze a DNA sample or more than one, different DNA samples, to determine whether the sample comes from one individual or two individuals. The present method requires very low amounts of DNA and can use partial sequences of DNA fragments. Partial sequences are analyzed for the presence of polymorphisms (e.g. SNP's) that can be mapped to a reference SNP map. The distance between similar SNPS, which are genetically linked, can be used to statistically determine a likelihood of identity of individuality in a sample.

19 Claims, 5 Drawing Sheets

METHOD FOR DETERMINING RELATEDNESS OF GENOMIC SAMPLES USING PARTIAL SEQUENCE INFORMATION

CROSS-REFERENCE TO RELATED APPLICATIONS

This application claims priority from U.S. Provisional Patent Application No. 62/013,734, filed Jun. 18, 2014, which is hereby incorporated by reference in its entirety, and is a U.S. national stage application of PCT/US2015/036250, having an international filing date of Jun. 17, 2015, the disclosure of which is incorporated herein by reference in its entirety.

STATEMENT OF GOVERNMENTAL SUPPORT

This invention was made with Government support under contract FOAPAL 443860-26764 awarded by the Smithsonian Institution. The Government has certain rights in this invention.

REFERENCE TO SEQUENCE LISTING, COMPUTER PROGRAM, OR COMPACT DISK

None.

BACKGROUND OF THE INVENTION

Field of the Invention

The present invention relates to the field of DNA analysis, in particular to DNA analysis to identify one or more unique individuals represented in a DNA sample.

Related Art

Presented below is background information on certain aspects of the present invention as they may relate to technical features referred to in the detailed description, but not necessarily described in detail. That is, individual compositions or methods used in the present invention may be described in greater detail in the publications and patents discussed below, which may provide further guidance to those skilled in the art for making or using certain aspects of the present invention as claimed. The discussion below should not be construed as an admission as to the relevance or the prior art effect of the patents or publications described.

Determining whether two DNA samples originate from the same individual is difficult when the amount of retrievable DNA is limited. In the field of Ancient DNA, DNA preservation and the amount of material available for extraction limit our ability to construct high-coverage shotgun sequencing libraries from historical samples. As a result, in two libraries prepared from the samples from the same individual, very few sequenced reads will overlap between libraries and even fewer will fall on polymorphic positions that can be used to verify their origin in a single individual.

Recent advances in high-throughput sequencing now allow for small DNA fragments to be extracted and sequenced from ancient or heavily degraded samples. DNA is now routinely extracted from bones, teeth, and hair from individuals that lived hundreds or thousands of years ago. Deep sequencing of well-preserved samples can yield many-fold coverage of the complete nuclear genome [1-3], but many more samples can offer only a low-coverage (<1x) view. This is due to several factors. First, the amount of endogenous DNA present varies greatly between samples and in most samples, endogenous DNA makes up only a small fraction of the extracted fragments. Deep sequencing and/or capture techniques can applied to enrich for human DNA, but this can be limited by a small starting number of intact fragments. In addition to this, some samples are limited by the material available for destructive sampling and extraction, e.g. single hairs or unique specimens. Low-coverage nuclear genomic sequence has provided key insights into human prehistory [4,5] and analysis methods designed specifically for low-coverage sequence data are required as more ancient and historical samples are sequenced. Although DNA has been used for human identification for decades, current methods are not readily applicable to extremely low-coverage genome sequence. In certain embodiments a genome fragment such as a particular chromosome or a mitochondrion could be studied. In other embodiments an entire genome will be used.

The most basic strategy for determining if two samples are from the same individual is to identify the alleles found at known polymorphic sites for each sample and compare the results. If the two samples are from the same individual, all genotypes of DNA tested should match with the exceptions of differences caused by measurement error, allelic dropout, or somatic mutation. Low sequence coverage makes this difficult. First, identifying an individual requires identifying specific alleles at known polymorphic sites. Reads from a low coverage sample must overlap polymorphic positions in order to find alleles (bases) that differentiate the individual from others. The majority of positions in the genome will not have any observations in a single low coverage library. Comparing two low-coverage libraries compounds this problem, as very few positions will have observations in both libraries. This limits direct comparisons of alleles in different libraries to a very small number of informative sites.

Identification methods that rely on a handful of specific variable lengths of repetitive sequences, like CODIS, may not be suitable to highly fragmented DNA, where these loci may not have been sampled or remain intact. Alleles at single nucleotide polymorphisms (SNPs) can be identified from small fragments. SNP-based forensic analyses rely on a relatively small set (50-80) of heavily curated SNPs and most of these markers would not be observed in low-coverage shotgun sequencing of the genome. Out of all of the loci used in forensic analyses, the mitochondrial sequence (mtDNA) is most easily applied to ancient DNA, as its high cellular copy number often allows for the complete sequence to be assembled from libraries with low nuclear coverage. However, this single loci provides limited information on only the matrilineal ancestry of an individual and has no power to differentiate between individuals that share the same mtDNA sequence. We present a method for determining whether low-coverage shotgun data from two samples are derived from the same individual.

BRIEF SUMMARY OF THE INVENTION

The following brief summary is not intended to include all features and aspects of the present invention, nor does it imply that the invention must include all features and aspects discussed in this summary.

The present invention comprises method for genotyping uncharacterized genomic DNA, based on limited sequence information of the genomic DNA in a sample, comprising: (a) obtaining a plurality of independent DNA sequences (e.g.

from different sequencing reads) containing identified polymorphic sites; (b) calculating a set of linkage disequilibrium ("LD") scores for a number of pairs of said polymorphic sites obtained in step (a), resulting in a set of LD scores indicating likelihoods that polymorphic sites in a given pair are linked on a chromosome and wherein LD scores are calculated in physical locations along a genome or individual being genotyped as to identity; and (c) preparing a compilation of scores from step (b), (d) wherein said compilation indicate a likelihood that the plurality of sequences are from a single individual or are from more than one individual, based on compiled LD scores. As described below, the present method can use inputs from sequencing a sample and using database of identified polymorphic sites. Such databases are known and publically available in genomic databases. Alternatively, they may be compiled by a user.

In certain aspects, the present methods comprise the use of uncharacterized genomic DNA from a variety of samples obtained in the field, including forensic samples such as human blood, hair root, saliva, semen or bone marrow sample. In certain aspects, the present methods comprise determination of whether a sample contains DNA from more than one individual; also, the method may use uncharacterized genomic DNA is from more than one sample.

The various methods described here in connection with the present invention may use polymorphic sites are selected from the group consisting of variable number tandem repeats (VNTRs); simple-tandem repeats, short tandem repeats (STRs); single nucleotide polymorphism (SNPs), human mitochondrial DNA (mtDNA) first hypervariable region (HVI) and second hypervariable region (HVII). As described further below, these polymorphic sites may be selected SNPs. The SNPS may be recorded in a publicly available archive containing chromosomal locations of SNPS within the archive. In certain aspects, the present methods comprise the use of SNPS that occur in unique subsequences within a genome. In certain aspects, the present methods comprise the use of SNPs occurs in at least one percent of a population. The various polymorphic sites that can be used will be identified in by genomic location by use of known database material, as described below.

In certain aspects, the present methods comprise analyzing a genomic sample by next generation sequencing methods. The methods in the invention described here may comprise a step of obtaining a plurality of independent DNA sequences further comprises the step of massively parallel sequencing said genomic DNA in the sample. In certain aspects, the present methods comprise obtaining a plurality of independent DNA sequences further comprises massively paralleling sequencing in a platform generating read lengths between 50 and 350 bp. In certain aspects, the present methods comprise sequencing comprises a step of randomly fragmenting genomic DNA in a sample. In certain aspects, the present methods comprise cases where limited sequence information is sequencing of between 1% and 10% of the genome or individual being genotyped as to identity.

In certain aspects, the present methods comprise methods of calculating probabilities of linkages of polymorphic sites determined by sequencing a sample. In certain aspects, the present methods comprise calculating a set of linkage disequilibrium ("LD") comprises sliding windows of polymorphisms located in proximity on a chromosome.

In certain aspects, the present methods comprise use of a plurality of genomic samples. The methods may comprise determining relatedness of a plurality of genomic sequences in a plurality of genomic samples, comprising: determining nucleotide sequence information from a first genomic sample and a second genomic sample, said sequence information including identified, mapped polymorphisms; comparing polymorphism information from step (a) with a reference set of mapped polymorphisms and obtaining linkage disequilibrium ("LD") values; and (c) using values obtained in step (b) to determine a likelihood that the first genomic sample and the second genomic sample are from the same individual, by comparing odds scores from a selection of comparison along the first genomic sample and the second genomic sample.

As described in this section, in certain aspects, the present methods comprise the analysis of genomic samples that are each human. Further, the methods may comprise the use of a likelihood is determined using LD information from a SNP database. The may also comprise use SNP linkage information that is obtained from the SNP genotypes contained in a genome project.

As described below, the present methods may be carried out with low sequence coverage. In certain aspects, the present methods comprise use of sequence information is less than 0.10× (10%) of any genome in the sample, or even as low as 0.5% coverage, and other ranges disclosed below.

In certain aspects, the present invention comprises hardware and software for carrying out the above methods. In certain aspects, the present methods are comprised in a computer program containing instructions for calculating a likelihood of genetic identity between two sets of sequence data, comprising: (a) calculating a set of linkage disequilibrium ("LD") scores for a number of pairs of said polymorphic sites obtained in step (a), resulting in a set of LD scores indicating likelihoods that polymorphic sites in a given pair are linked on a chromosome and wherein LD scores are calculated in physical locations along a genome being genotyped as to identity; and (b) preparing a compilation of scores from step (a), wherein said compilation indicate a likelihood that the plurality of sequences are from a single individual or are from more than one individual, based on compiled LD scores.

DETAILED DESCRIPTION OF THE PREFERRED EMBODIMENT

Overview

Figure 1A:
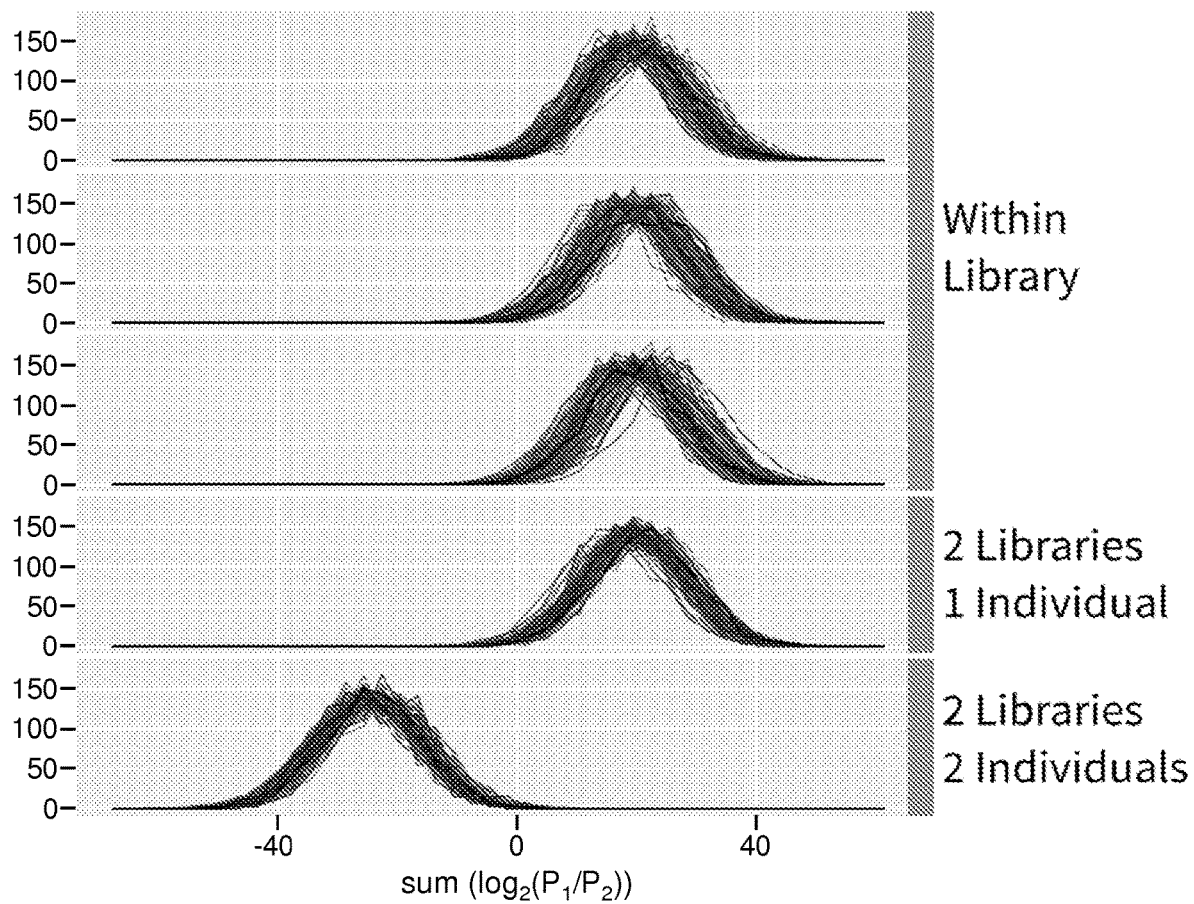
FIG. 1A, 1B, 1C is a set of graphs showing comparisons of simulated libraries. It is shown that using the methods of the present invention, simulated libraries made from the same individual can be distinguished from those made from different individuals.

Described herein is a method for assessing whether two low-coverage (e.g. <0.01×, libraries are consistent with originating in the same individual or two individuals using linkage disequilibrium information obtained from a reference panel of individuals. These reference panels can be obtained from publicly available data that describes the genetic correlations observed within human populations. We compare observed alleles at closely linked polymorphic sites (e.g. single nucleotide polymorphisms, SNPs) to determine whether they are consistent with the patterns of linkage present in the reference panel. Robustness of the method is shown by performing coalescent simulations (See, Arenas, M. and Posada, D. (2007) Recodon: Coalescent simulation of coding DNA sequences with recombination, migration and demography. BMC Bioinformatics 8: 458) to assess the power of the method to distinguish between pairs of simulated low-coverage libraries derived from a single individual or two individuals using a simulated reference panel. It has been found that the method can distinguish between these two cases and retains power when the reference panel is made up of individuals from a diverged population.

The present invention has been implemented by the use of known, mapped SNPs. SNP genotypes from the 1000 Genomes Project may be further obtained from http(colon slash slash) www (dot) 1000genomes.org.

SNP genotyping is the measurement of genetic variations of single nucleotide polymorphisms (SNPs) between members of a species. It is a form of genotyping, which is the measurement of more general genetic variation. SNPs are one of the most common types of genetic variation. A SNP is a single base pair mutation at a specific locus, usually consisting of two alleles (where the rare allele frequency is >1%). SNPs are found to be involved in the etiology of many human diseases and are becoming of particular interest in pharmacogenetics. Because SNPs are conserved during evolution, they have been proposed as markers for use in quantitative trait loci (QTL) analysis and in association studies in place of microsatellites. The use of SNPs is being extended in the HapMap project, which aims to provide the minimal set of SNPs needed to genotype the human genome. SNPs can also provide a genetic fingerprint for use in identity testing. The increase in interest in SNPs has been reflected by the furious development of a diverse range of SNP genotyping methods.

Linkage Disequilibrium (LD) is further described in http (colon-slash-slash) snpinfo.niehs.nih (dot) gov/snpinfo/guide.htm.

Useful sequencing methods for the present samples (e.g. forensic DNA samples or tumor samples in FFPE (formalin-fixed paraffin-embedded tissue) can be carried out using a variety of next-generation sequencing methods. These are described, e.g. in U.S. Pat. No. 8,685,678, "Increasing confidence of allele calls with molecular counting," describing relevant definitions to the present application, and describing that: "Next-generation sequencing" (NGS) as used herein refers to sequencing technologies that have the capacity to sequence polynucleotides at speeds that were unprecedented using conventional sequencing methods (e.g., standard Sanger or Maxam-Gilbert sequencing methods). These unprecedented speeds are achieved by performing and reading out thousands to millions of sequencing reactions in parallel. NGS sequencing platforms include, but are not limited to, the following: Massively Parallel Signature Sequencing (Lynx Therapeutics); 454 pyro-sequencing (454 Life Sciences/Roche Diagnostics); solid-phase, reversible dye-terminator sequencing (Solexa/Illumina); SOLiD technology (Applied Biosystems); Ion semiconductor sequencing (Ion Torrent); and DNA nanoball sequencing (Complete Genomics). Descriptions of certain NGS platforms can be found in the following: Shendure, et al., "Next-generation DNA sequencing," Nature, 2008, vol. 26, No. 10, 1135-1145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11(3):333-43; and Zhang et al., "The impact of next-generation sequencing on genomics", J Genet Genomics, 2011, 38(3):95-109.

The present methods may use low coverage sequencing. See for further details, Tutorial: Low Pass Sequence Analysis, http (colon slash slash) genome.sph.umich (dot) edu/wiki/Tutorial:_Low_Pass_Sequence_Analysis. Also, Carpenter et al., "Pulling out the 1%: Whole-Genome Capture for the Targeted Enrichment of Ancient DNA Sequencing Libraries," AJGH, Volume 93, Issue 5, p 852-864, 7 Nov. 2013.

Shotgun sequencing is a laboratory technique for determining the DNA sequence of an organism's genome. The method involves breaking the genome into a collection of small DNA fragments that are sequenced individually. A computer program looks for overlaps in the DNA sequences and uses them to place the individual fragments in their correct order to reconstitute the genome.

Various types of random sequencing of the sample(s) may be used, as noted above. See, also, Metzker, "Sequencing technologies—the next generation," Nat. Rev. Genetics, 11:31-46 (2010).

Some amount of shotgun (random) DNA sequence is generated from two sources. These sources could be forensics samples, historical samples, etc. The DNA sequence collected is then compared, using known patterns of linkage from known data sources. These patterns make a prediction about what DNA sequence variants will be seen in one sample given data from another sample under two scenarios: (1) the two samples derive from the same person (2) the two samples derive from different people. In this way, this method can determine if two samples come from the same or different people. In a related implementation, the method can determine the degree of relatedness between the two samples (full siblings, half siblings, parent/offspring, etc.).

The present method works directly on observed bases in mapped reads for assessing whether two extremely low coverage shotgun sequence libraries are consistent with originating from a single person, given a reference population. Rather than relying on a small number of loci to make this determination, this method takes advantage of millions of single-nucleotide polymorphisms (SNPs) previously identified in population surveys. Since majority of these positions will not be observed in a low-coverage library, our method does not rely on direct comparison of SNP alleles but instead uses a likelihood model to examine pairs SNPs in linkage disequilibrium to determine whether the observations are consistent with a single individual. To assess the utility of this approach, we tested it using simulated data and down sampled high-coverage sequence data. We demonstrate that a few hundred thousand reads is sufficient to differentiate between libraries that originate from the same and different individuals.

As explained below, the present invention comprises computer-assisted analysis. The systems of the present disclosure may include a display (e.g., an LCD, LED, or other suitable display). In certain aspects, the instructions further cause the processor to display the likelihood that a given sample or samples originated from one individual or from more than one individual. According to certain embodiments, the instructions may further cause the processor to calculate and display odds of identity within a nucleic acid (e.g.DNA) sequencing library. The results of the comparison of libraries and methods for identification similarities of low coverage sequence information may be prepared on a computer-readable medium. The computer-readable medium (or processor-readable medium) is non-transitory in the sense that it does not include transitory propagating signals per se (e.g., a propagating electromagnetic wave carrying information on a transmission medium such as space or a cable). The media and instructions may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Definitions

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well-known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

Ranges:

For conciseness, any range set forth is intended to include any sub-range within the stated range, unless otherwise stated. As a non-limiting example, a range of 0.01 to 1 is intended to cover covers 0.1 to 0.5, 0.6 to 00.1 to 0.5, 0.2 to 0.5, etc.

The term "about" has its ordinary meaning of approximately and may be determined in context by experimental variability. In case of doubt, the term "about" means plus or minus 5% of a stated numerical value.

The term "linkage disequilibrium" (LD) is used in the conventional sense to refer to the nonrandom association of alleles at different loci.

The term "polymorphic site" or "polymorphism" refers to genetic variants that may be found among individuals in a population. The term includes variable number tandem repeats (VNTRs); simple-tandem repeats, or short tandem repeats (STRs); single nucleotide polymorphism (SNPs), human mitochondrial DNA (mtDNA) first hypervariable region (HVI) and second hypervariable region (HVII). A polymorphism is to be distinguished from a mutation. A mutation is defined as any change in a DNA sequence away from normal. This implies there is a normal allele that is prevalent in the population and that the mutation changes this to a rare and abnormal variant.

In contrast, a polymorphism is a DNA sequence variation that is common in the population. In this case, no single allele is regarded as the standard sequence. Instead there are two or more equally acceptable alternatives. The arbitrary cut-off point between a mutation and a polymorphism is 1 percent. That is, to be classed as a polymorphism, the least common allele must have a frequency of 1 percent or more in the population. If the frequency is lower than this, the allele is regarded as a mutation.

As used herein, the term "single nucleotide polymorphism", or "SNP" for short, refers to a phenomenon in which two or more alternative alleles (i.e., different nucleotides) are present at a single nucleotide position in a genomic sequence at appreciable frequency (e.g., often 1%) in a population. In some cases, SNPs may be present at a frequency less than 1% in a population. As used herein, the term SNP may include these "rare SNPs" (present at a frequency less than 1% in a population) or even "single nucleotide variants" (SNVs) that have only been detected in one or a few samples to date.

As used herein, the term "SNP site" denotes the position of a SNP in a genomic sequence. A SNP site may be indicated by genomic coordinates. The nucleotide sequences of hundreds of thousands of SNPs from humans, other mammals (e.g., mice), and a variety of different plants (e.g., corn, rice and soybean), are known (see, e.g., Riva et al 2004, A SNP-centric database for the investigation of the human genome BMC Bioinformatics 5:33; McCarthy et al 2000 The use of single-nucleotide polymorphism maps in pharmacogenomics Nat Biotechnology 18:505-8) and are available in public databases (e.g., NCBI's online dbSNP database, and the online database of the International HapMap Project; see also Teufel et al 2006 Current bioinformatics tools in genomic biomedical research Int. J. Mol. Med. 17:967-73).

As used herein, the term "SNP sequence" refers to is a naturally-occurring nucleotide sequence that contains a SNP site. Since at least two alleles my exist at a given SNP site, at least a pair of SNP sequences correspond to each SNP site, both of which contain the same flanking sequences, but the nucleotide at the SNP site differs. A SNP sequence can be of any length, and in particular embodiments may be up to 5, 10, 15, 20, 25, 30, 35 or 40 nucleotides or more, e.g., up to 50-80 nucleotides or more. In particular embodiments, the sequences that flank a SNP site on either side may be at least 2, 3, 4, 5, 6, 7, 8, 9, 10, 11, 12, 13, 14, 15, 16, 17, 18, 19, 20 nucleotides long, or more, e.g., 15-30 or 15-40 nt, or any range in between (such as 3-15, 5-12, 9-16, etc. Similarly, 0.1%-10% includes ranges of 0.1-0.5, 0.2-0.6, 2-7, etc.

The term "library" is used herein to refer to a portion of a nucleic acid sample that is treated and used for analysis. For example, a genomic DNA library may be prepared for next-generation sequencing using various kits available from sequencing manufacturers. The Illumina® TruSeq Nano DNA Library Prep Kit (http(colon-slash-slash) www (dot) illumine (dot)com/products/truseq-nano-dna-library-prep-kit.html describes how a workflow delivers 16 sequencing-ready libraries, eliminating almost all manual steps. In addition, digital microfluidics requires less DNA input, enabling excellent performance from 25-75 ng of gDNA. In additional, successful libraries have been demonstrated with DNA inputs ranging from 1-100 ng, up to 10 fold lower than required by manual protocols.

The term "coverage" in terms of sequence coverage of a nucleic acid molecule is used in its conventional sense. In general, it is the number of times that a given nucleotide in the sequence has been read, or sequenced. A number like 80× coverage means that, on average, each nucleotide will have been sequenced 80 times. It is important to note that this is only an average. Sequence coverage is further explained in Sims et al., "Sequencing depth and coverage: key considerations in genomic analyses," Nat. Rev. Gen. 15:121-132 (2014). By way of further example, a coverage 0.5%× means that, as to the DNA molecules being sequenced, each base position will be observed 0.005 times. As described herein, the analysis of low coverage sequence libraries means between a lower limit of between about 0.1%× (0.001×) and 0.5%× (0.005). The present methods perform at higher coverage levels that are nonetheless below those useful with other known methods, e.g. coverages less than 10%× (0.1×). Coverage is related to the idea that a nucleic acid sample is being sequenced in a random fashion, rather than targeting a specific sequence region. Further, the concept of coverage is related here to the ability to obtain a high coverage of sequencing. For example, low sequence coverage may result from a highly degraded sample, or a very small sample, where there is less than an amount of DNA necessary of other analysis methods. By way of example, an STR match has been reported to require a nanogram of DNA, whereas the present methods may be carried out on less, as described below.

The term "DNA sample" as used in the present methods may be a sample obtained in a laboratory or in the field, such as a blood spot, a hair root, saliva, semen, bone marrow, urine, cheek swab, etc.

As used herein, the term "genotyping" is used in its conventional sense to refer to the process of determining differences in the genetic make-up (genotype) of an individual by examining the individual's DNA sequence using biological assays and comparing it to another individual's sequence or a reference sequence. It reveals the alleles an individual has inherited from their parents (See Wikipedia, "Genotyping").

The term "VNTR" is used in its conventional sense to refer to variable number tandem repeats, which are described further, e.g. in Devlin et al., "Estimation of allele frequencies for VNTR loci," Am J Hum Genet. 1991 April; 48(4): 662-676.

The term "STR" is used in its conventional sense to refer to simple-tandem repeats or short tandem repeats, described further, e.g. in Doi et al., "Rapid detection of expanded short tandem repeats in personal genomics using hybrid sequencing," Bioinformatics. 2014 Mar. 15; 30(6): 815-822.

The term "first hypervariable region (HVI) and second hypervariable region (HVII)" is used in its conventional sense to refer to mitochondrial hypervariable regions as described, e.g. in Divne et al. "Forensic Casework Analysis Using the HVI/HVII mtDNA Linear Array Assay," J. Forsen Sci. 50(3) 1-7, Paper ID JFS2004505 (2005).

Also, it is known that a unique sequence in the human genome (as described in Venter et al., "The Sequence of the Human Genome" Science 291:1304-1351(2001),) can be identified by only about 10-20 bases; the probability that a sequence 20 bases will occur randomly has been estimated as being about $9 \times 10^{-9}$.

The term "massively parallel sequencing" is used in its conventional sense to refer to as any of several high-throughput approaches to DNA sequencing using the concept of massively parallel processing; it is also called next-generation sequencing (NGS) or second-generation sequencing. Some of these technologies are commercially available from Illumina Corp., Roche 454, Ion Torrent (Life Technologies) and others. These technologies use miniaturized and parallelized platforms for sequencing of 1 million to 43 billion short reads (50-400 bases each) per instrument run. (Wikipedia "Massively parallel sequencing; see also Moorthie et al., "Review of massively parallel DNA sequencing technologies," Hugo J. 5(1-4): 1-12 (2001).) An example of massively parallel sequencing is a commercial product available from Illumina Inc., San Diego Calif. In this (and other platforms) During DNA sequencing, the bases of a small fragment of DNA are sequentially identified from signals emitted as each fragment is re-synthesized from a DNA template strand. Next-generation sequencing (NGS) extends this process across millions of reactions in a massively parallel fashion. The slide is flooded with nucleotides and DNA polymerase. These nucleotides are fluorescently labelled, with the color corresponding to the base. They also have a terminator, so that only one base is added at a time. The slide is flooded with nucleotides and DNA polymerase. These nucleotides are fluorescently labelled, with the color corresponding to the base. They also have a terminator, so that only one base is added at a time. Computers are then used to detect the base at each site in each image and these are used to construct a sequence. All of the sequence reads will be the same length, as the read length depends on the number of cycles carried out. In Illumina sequencing, 100-150 bp reads are used. Since massively paralleling sequencing methods typically have limited read lengths, the methods will general a large number of independent sequences that are assembled as described above. Each independent sequence originates from a different DNA molecule in the sequencing library.

The term "LOD score" is used in the conventional sense to refer to the logarithm (base 10) of odds that is a statistical test for linkage analysis. It is further described in Morton, "Sequential tests for the detection of linkage". American Journal of Human Genetics 7 (3): 277-318 (1955). The LOD score compares the likelihood of obtaining the test data if the two loci are indeed linked, to the likelihood of observing the same data purely by chance. Positive LOD scores favor the presence of linkage, whereas negative LOD scores indicate that linkage is less likely. By convention, a LOD score greater than 3.0 is considered evidence for linkage, as it indicates 1000 to 1 odds that the linkage being observed did not occur by chance. On the other hand, a LOD score less than −2.0 is considered evidence to exclude linkage.

General Methods and Materials

The present methods provide a technical solution for the problem of analyzing nucleic acid molecules in a sample wherein there may be more than one individuals contributing to the sample and, further, there is insufficient sample to obtain more than a small fraction of the sequence information present. The present method is easily illustrated in a forensic situation where one wishes to match nucleic acids (DNA is used by way of example) from one hair (for example) with another hair. Also, the method may be used to determine if a recovered blood sample contains from blood of a single individual or more than one individual. The method comprises obtaining sequence information from known sequencing methods, even though very incomplete sequence information can be obtained. For example, in certain situations, only between about 1% and 10% of a genome (e.g. human genome, having $3 \times 10^9$ base pairs) can be sequenced from a sample. Small amounts of suitable sequencing sample can still be prepared in sequencing libraries for use in next generation sequencing methods.

The present methods have been applied to libraries made from extracts from several different samples all reportedly from the same individual. The certainty that these samples actually originate from this individual varies from sample to sample. Here we describe a test to see whether two low-coverage libraries are consistent with originating from a single individual.

There are factors that complicate this. First, we cannot exclude the possibility that two individuals share the same mitochondrial haplotype. The only way to differentiate between two individuals in this case is to examine data from the autosomes. Second, the available sequence coverage may be very low (<0.1×).

Given sufficient depth, this question could be answered easily by examining the coverage of polymorphic sites between libraries. However, it is unlikely that we will ever have enough coverage to do this. Furthermore, the extremely low coverage we have available means that any base we observe will likely only be observed once.

Description of Analysis:

Since we require evidence from the autosomal genome and we cannot rely on multiple observations of any base, we will use pairs of observations of neighboring SNPs. Using frequency and linkage disequilibrium (LD) information from the 1000 Genomes project, we can calculate the probability of observing two SNP alleles together under two simple models, one where both reads come from the same individual and one where the reads are from two individuals.

$$P_1(A \wedge B) = \tfrac{1}{2} f(A \wedge B) + \tfrac{1}{2} f(A) f(B) \quad \text{FORMULA 1A}$$

$$P_2(A \wedge B) = f(A) f(B) \quad \text{FORMULA 1B}$$

Using the above FORMULA 1A, $P_1$ represents the probability of observing alleles A and B together if both observations originate in the same diploid individual. This is found using the frequency of A and B appearing together estimated from the reference panel ($f(A \wedge B)$) and the frequencies of A and B in the reference panel ($f(A), f(B)$). We assume that we are equally likely to make observations from each chromosome, so there is an equal probability of observing bases from the same chromosome (linked) and from different chromosomes (unlinked). Similarly in FORMULA 1B, $P_2$ represents the probability of observing alleles A and B on independent (unlinked) chromosomes. Here the probability of observing both alleles is the product of their frequencies in the population. Again, we estimate these frequencies using the reference panel of haplotypes. As described below, these formulas are calculated (preferably using a computer) a log odds ratio for all linked pairs of SNPs.

Two loci are in linkage disequilibrium (LD) if their alleles are not randomly associated [11]. This non-random association implies that observing the allelic state of one locus provides some information about the state of the other. Similarly, our approach is based on the idea that observations made in one sample should not provide information about bases in another sample if the two individuals are unrelated. In other words, the probability of observing one combination of alleles at linked loci should be dependent on the allele frequencies if the two alleles originate from different chromosomes. However, if they both observations are made from the same chromosome, the probability of the observation is the frequency of that haplotype.

In our approach, we explicitly model allele and haplotype frequencies using a reference panel of phased haplotypes that represent the population from which our samples were drawn.

We consider pairs of SNPs within close physical proximity of each other where a base has been observed. We compare the probabilities of observing the first base given the observation of the second under two simple models. The first represents the case where the two bases have been drawn from independent chromosomes, so the probability of the observation is the frequency of the base in the population and is independent of the first base. The second model represents the case where the two bases where drawn from the same diploid individual, where there is an equal chance the two bases come from the same chromosome or independent chromosomes. The two models are compared as a log-likelihood ratio (LLR).

We aggregate the LLRs for pairs of SNPs by sampling pairs from sliding windows across each chromosome to avoid the effects of linkage and to mitigate the influence of heavily sampled regions. We model the genome-wide LLR at a random variable and build an empirical distribution by sampling across the genome many times. Positive values indicate support for the single diploid individual model, while negative values indicate the observations are more likely to be from two independent individuals.

Figure 3:
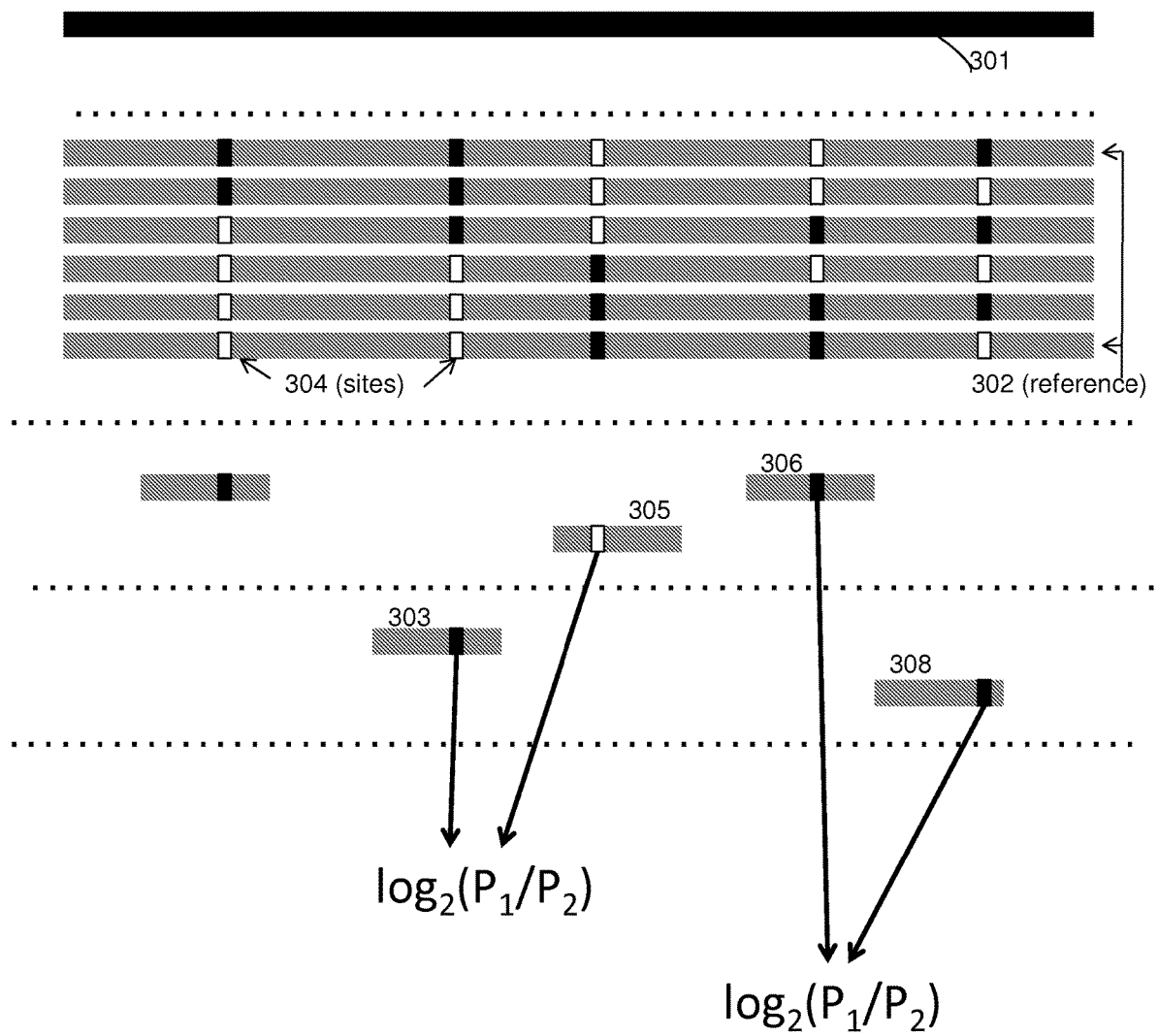
FIG. 3 is a diagrammatic representation of a method for calculating and aggregating log-likelihood ratios using sequence markers (SNPs) mapped in individual fragments and a reference panel of haplotypes.

This method is illustrated schematically in FIG. 3. A representation of a chromosome or related contiguous nucleic acid fragment is shown at 301. A reference panel of phased haplotypes (shown at 302) describes the known variants associated with this nucleic acid fragment (referred to for illustration purposes as a chromosome). Note that these variants, referred to and for illustration purposes as SNPs, are not randomly associated with each other in the phased polymorphism population (304) as mapped in the reference 302. In this illustration, 5 known SNPs are detected; data from SNPs 303, 305, 306 and 308 are used in two pair-wise calculations. Reads from two samples are mapped to the chromosome and alleles are observed at variant sites (e.g. 303 and 305). Pairs of observations are grouped for purpose of analysis and for calculating log-likelihood ratios using the reference panel. This illustration shows a single window or region of a chromosome where several comparisons of SNP pairs could be made (303-305 and 306-308). Any number of sliding windows (overlapping or non-overlapping) of various physical sizes on the chromosome can be used. For each window, a single pair comparison and calculated LLR is drawn to represent the window. LLR values are aggregated across windows by summation. Because multiple pair comparisons are available for each window, this step can be repeated using a bootstrapping approach The method can be applied to sets of base observations made within a single sample and between two samples. Within-sample comparisons are used to examine how consistent the observations made from a single sample are with a single diploid individual, given the reference population. Positive LLR values indicate that the sample is consistent with a diploid individual that originated from a population closely related to the reference panel. Negative LLR values or values not significantly different from zero can be the result of the reference panel being too distantly related from the sample individual or the sample itself being a mixture of fragments from more than one individual. Between-sample comparisons are made to examine how consistent two sets of base observations are with originating in a single diploid individual. Ideally, each sample should be compared with itself first, before comparing it with another library.

The method begins with a SNP reference panel of haplotypes from a population chosen based on a priori knowledge or previous analyses to best represent the population from which the samples originated. For each sample, we examine reads that overlap SNP positions from the panel to identify the base at that position. Bases that do not match one of the two alleles from the reference panel are discarded.

Observations for positions where multiple reads map are omitted. The majority of positions will have no observation.

In selecting pairs of SNPs used in calculating LLR values, one should consider the proximity of the SNPs, the minor allele frequency, and the possible misinformation caused by damage bases. A variety of SNP databases can be used in analyzing sequence results from the present method. In addition the present method may use only SNPs that are informative to the present method. As of Jun. 15, 2015, the National Center of Biotechnology Information's dbSNP databases contains over 90 million validated SNPs found in the human genome (http(colon slash slash) www (dot) ncbi.nlm.nih.gov/projects/SNP/snp_summary.cgi?view+summary=view+summary&build_id=144). SNPs used by this method should have minor alleles found at low to intermediate frequencies so that linkage disequilibrium can be identified and quantified with confidence. Presently used SNPs preferably are uniquely mapped to the human genome. These may be selected by identifying SNPs that occur in unique base pair contexts in the human reference genome. For example, this can be achieved using a database such as the UCSC genome browser and the Duke 35-mer Mapability track to select SNPs that occur in unique 35 base pair segments. Also, SNPs that represent transversions rather than transitions are preferred, to avoid errors caused by DNA damage or multiple mutation hits that may occur with transition mutations.

Next, we find all pairs of SNPs between the two samples within a specified distance on the chromosome. This includes a minimal distance to ensure that the two base observations are not made from the same read in within-library comparisons. For each pair we calculate the probability of that observation under two models. The first represents the probabilities of observing this combination of alleles in a diploid individual. FORMULA 1A may be written as:

$$P_1(A \wedge B) = \tfrac{1}{2} f(A \wedge B) + \tfrac{1}{2} f(A) f(B)$$

The second represents the two observations originating from two unrelated individuals and models the two observations as independent and based solely on the frequencies of each allele in the population. FORMULA 1B can be written as $$P_2(A \wedge B) = f(A) f(B)$$

These two models are compared as a log-likelihood ratio, which is calculated by:

$$\gamma(A, B) = \log_2 \frac{P_1(A \wedge B)}{P_2(A \wedge B)}$$

Log-likelihood ratios are aggregated across the entire genome by summation of $\gamma$ for pairs of SNPs from sampled from windows a set size.

$$\Lambda(S) = \sum_{(A,B) \in S} \gamma(A, B)$$

Simulations:

Coalescent simulations were performed in order to test the method free of base errors and under various demographic scenarios. The coalescent simulator was used [16] to simulate diploid individuals and population reference panels of haplotypes for comparison. Segregating sites with minor allele frequencies lower than 10% were removed. For diploid individuals, we simulated base observations from low-coverage sequencing by drawing a single allele from segregating sites randomly chosen at a rate of 0.01. This process was repeated to construct multiple observation sets per individual.

The single simple population model used a constant effective population size of 10,000. The second model, representing the reference population and samples originating in distinct populations, simulated an ancestral population of 10,000 that split 100, 500, 1000, 2000, and 4000 generations ago into two equal sized populations of 10,000 each. The model of recent human history was based off of parameters inferred by Gutenkunst et al. [12] (see SOM).

Reference Panels:

Reference panels were constructed of single nucleotide polymorphisms (SNPs) using the 1000 Genomes Project Phase 1 data set [14]. We used statistically phased SNP genotypes. Based on prior knowledge of the individual's ancestry one may choose individuals from one or more subpopulations for a reference panel.

The SNP markers were chosen to meet some basic requirements. SNPs must be polymorphic in our reference panel but it is not clear what the minimum minor allele count should be. Rare alleles represent the majority of our available markers, but they are not as informative at common alleles in strong LD. Furthermore, it is difficult to confidently describe the linkage between two alleles when only a few observations are available. A balance must be struck that allows for many informative pairs to be observed throughout the genome. We filtered for biallelic SNPs that were polymorphic in the target population (CEU, GBR, etc.) with a minimum minor allele count of 10. SNPs must occur in uniquely mapping regions of the genome. To avoid errors from mismapped reads, we restricted our panels to sites where all overlapping 35 mers are unique across hg19 according to the Duke Mapability track on the UCSC Genome Browser. In other words, we filtered for SNPs that occur in unique 35-mers. Finally, to avoid errors caused by DNA damage for historic samples, we only consider SNPs that represent transversion mutations (no C,T or A,G polymorphic sites).

EXAMPLES

Example 1: Results from Simulations

Figure 1B:
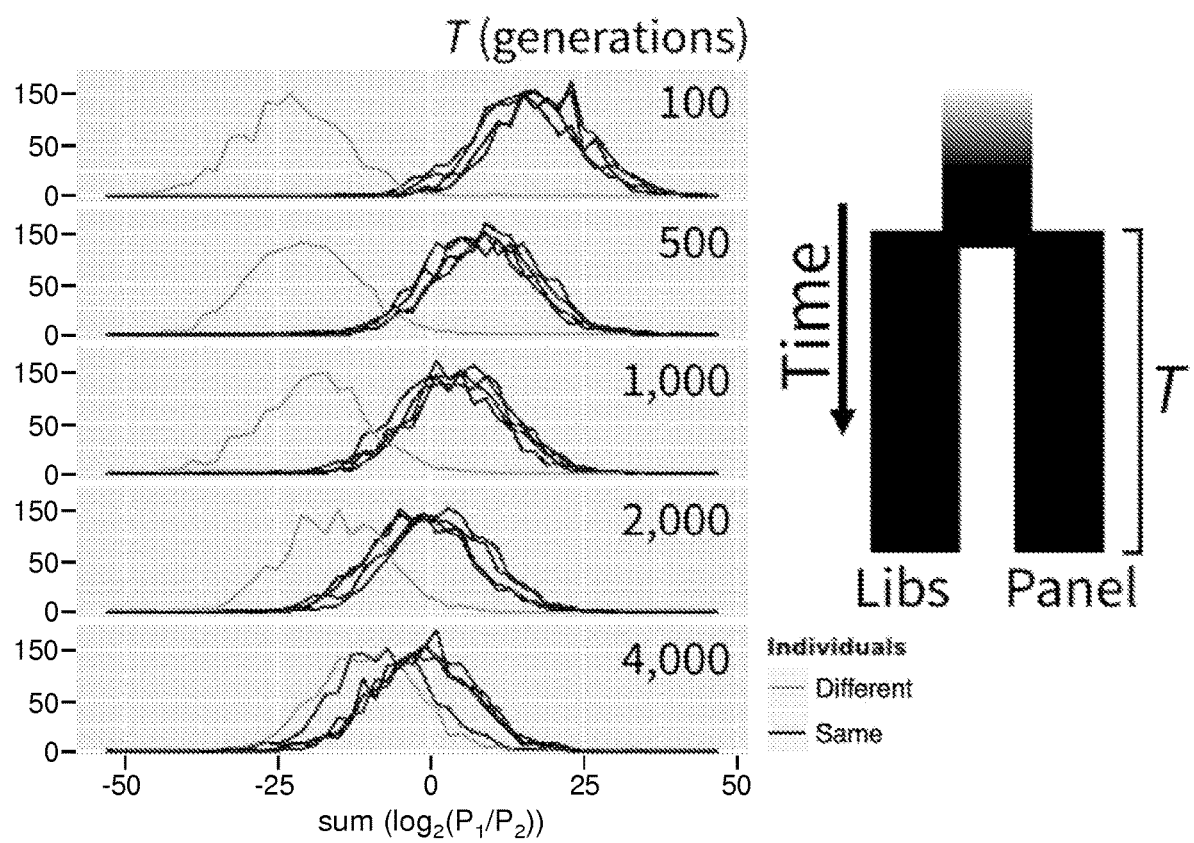

We simulated sets of single allele observations from diploid individuals and panels of reference haplotypes using coalescent simulations to test our method under various demographic scenarios free from observation errors. Under a simple demographic model of a single population of constant size (Ne=10,000), we found our method can consistently distinguish between two single allele observation sets that originate from the same or different individuals (FIG. 1A) when the reference panel and diploid individuals are drawn from the same population. Thus, sets of base observations made from the same diploid individual are distinguishable from those made from different individuals. Genotypes for diploid individuals and a reference panel of haplotypes were simulated under a simple demographic model of a constant effective population size of 10,000. Sets of base observations (libraries) were simulated by drawing random alleles from segregating sites chosen at a rate of 0.01, approximating 1%× coverage of the genome. The simulation was repeated 100 times with each line in the plot representing one comparison. In the case where the sampled individuals are from a population related to the reference population, it is still possible to differentiate between samples that come from one individual or two, but this becomes increasingly difficult as the number of generations since the split of these populations increases (FIG. 1B). In other words, comparisons made between the same and different individuals can still be distinguished when the reference panel is drawn from a related but diverged population. Under a demographic model where the diploid individuals are drawn from a distinct population related to the reference panel's population, sample pairs that originate from different diploid individuals can still be identified. As the time separating the two populations increases and the patterns of linkage disequilibrium diverge, the power to discern between one and two individuals decreases.

Figure 1C:
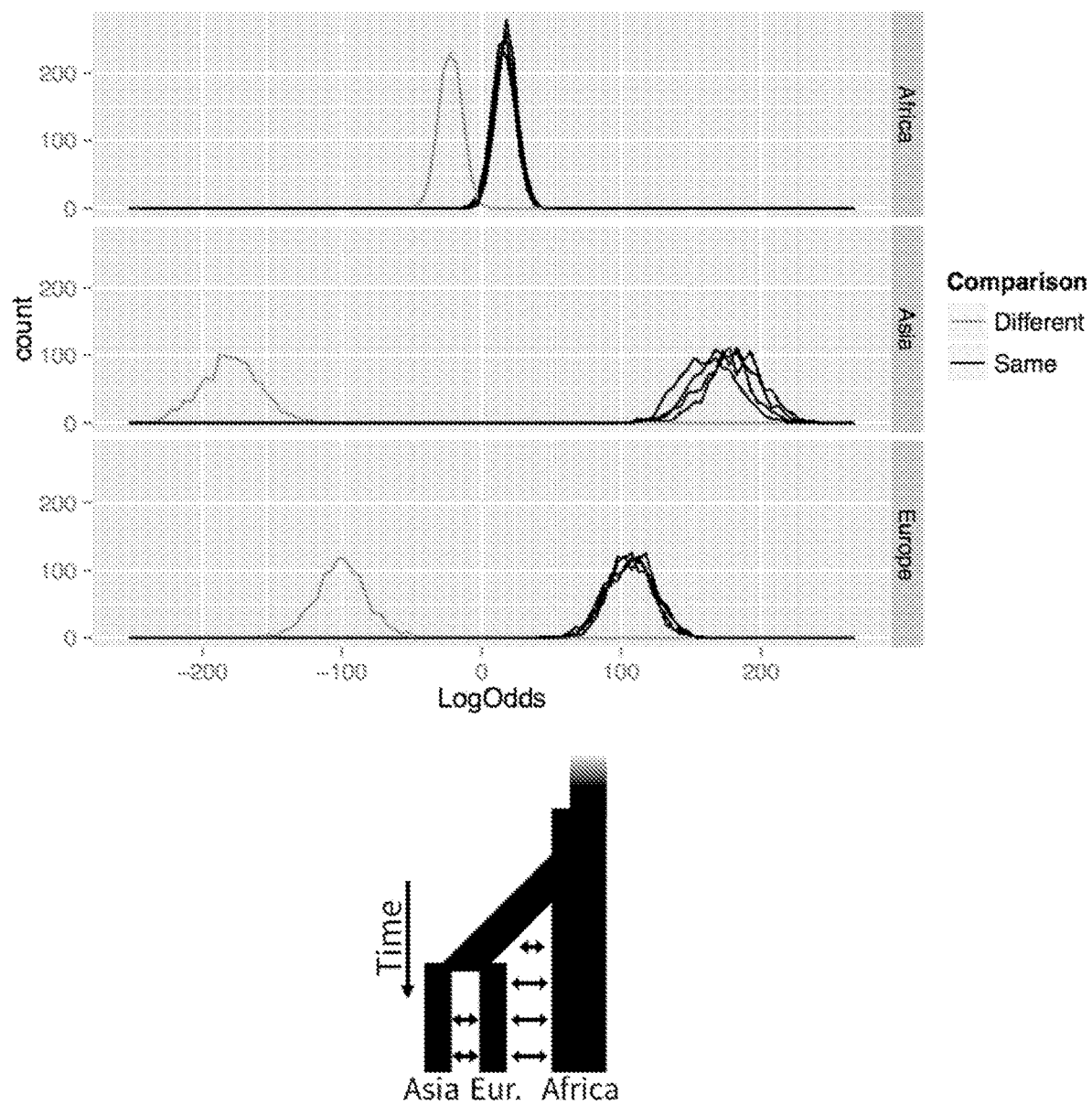

To test this method on a realistic demographic model for humans, a demographic history was simulated based on parameters inferred from SNP frequency data[12]. We simulated diploid individuals and reference population panels for three subpopulations representing subpopulations sampled from Africa, Asia and Europe. Importantly, this model features historical bottlenecks that increase and restructure LD in the effected subpopulations. Simulated libraries that were made from the same individual can be distinguished from those made from different individuals when the individuals and reference panel were drawn from the same subpopulation; in other words, comparisons made within each subpopulation can differentiate between samples that come from one or two individuals (FIG. 1C). We also found that the increased LD in subpopulations affected by bottlenecks offers more power in these comparisons; subpopulations with higher levels of linkage disequilibrium (for example, non-Africans) offer more information that can be used to make the comparisons. We also found that these events also limit the power of comparisons where the samples and the reference population are drawn from distinct subpopulations. This highlights the importance of choosing a suitable reference panel.

Example 2: Results from Read Data

To test our method on extremely low-coverage shotgun sequencing data, we obtained read data from a European male (NA12891) and a European female (NA12892) sequenced as part of Illumina's Platinum Genomes (http (colon/slash slash) www (dot) illumina(dot) com/plat-inumgenomes/) from the National Center for Biotechnology Information Sequence Read Archive (http(colon slash slash www(dot) ncbi.nlm.nih.gov/sra/, accession ERR194160 and ERR194161). We sampled reads without replacement to approximate 0.01%, 0.1%, 0.5%, 1.0%, and 5.0%× coverage of the nuclear genome to generate two sets at each coverage level for both individuals. Only the forward read (101 bp) were used from each read pair. Reads were mapped to the human reference genome (hg19) using bwa [13]. Reference panels were constructed using statistically-phased haplotypes from the 1000 Genomes Project phase 1 data [14]. Only biallelic single base substitutions were included in the panels. Base observations were made from the mapped reads using Samtools software program suite (using samtools mpileup) after coverage, map quality and base quality filtering [15].

Figure 2:
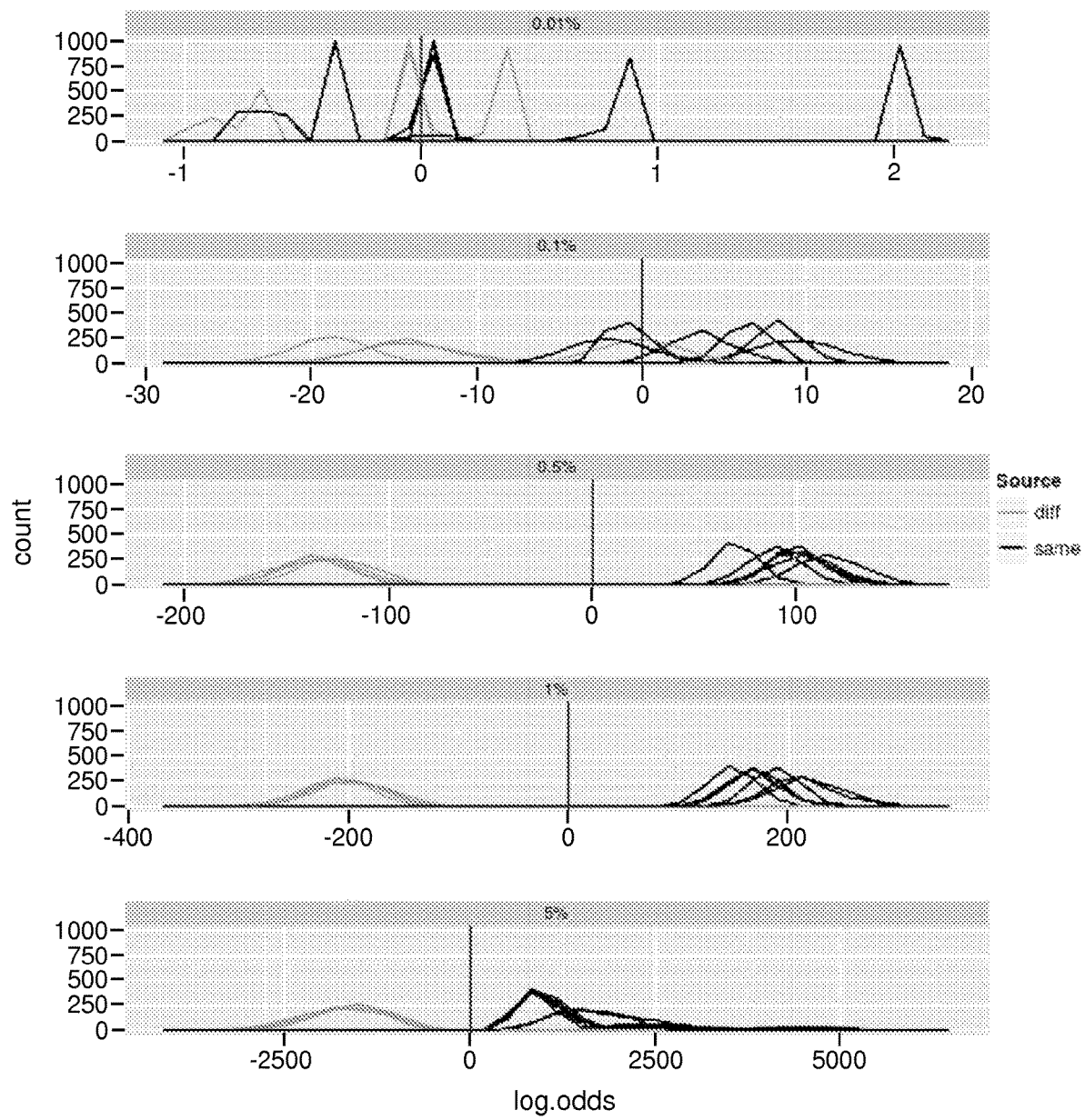
FIG. 2 is a set of graphs showing results from base observations made from down-sampled human sequencing data. Using the methods of the presently disclosed invention, it is possible to discern if two libraries (read subsets), at low coverage levels, e.g. less than 10% coverage, but preferably more than 0.5% coverage of the genome or genome portion under study.

Each sample was compared to itself and to the other three at the same coverage level using SNP pairs separated by 1 to 50 Kb and by sampling pairs by 100 Kb windows (FIG. 2). At the lowest coverage level, 0.01%, comparisons were not possible since very few pairs were found in close proximity due to the low observation density. At 0.1%× coverage, the distributions can be seen separating away from 0, with the comparisons made between the same individuals and comparisons between different individuals trending towards positive and negative respectively. With coverage levels 0.005 fold and higher, we have found that comparisons between the same and different individuals are distinct and easily differentiable. Thus, at coverage levels ≥0.5%×, it can easily be discerned if two libraries (read subsets) originated in the same individual or different individuals, but at coverage levels ≤0.1%×, it is difficult to distinguish between the two cases with the parameters used in this example.

Accordingly, the present examples show that non-overlapping sets of sparse single-base observations at SNP sites can be compared using a reference panel. The method also can be used to calculate a relationship coefficient between two samples.

REFERENCES

1. Meyer M, Kircher M, Gansauge M-T, Li H, Racimo F, Mallick S, Schraiber J G, Jay F, Prüfer K, de Filippo C, Sudmant P H, Alkan C, Fu Q, Do R, Rohland N, Tandon A, Siebauer M, Green R E, Bryc K, Briggs A W, Stenzel U, Dabney J, Shendure J, Kitzman J, Hammer M F, Shunkov M V, Derevianko A P, Patterson N, Andres A M, Eichler E E, et al.: *A high-coverage genome sequence from an archaic Denisovan individual. Science* 2012, 338:222-6.
2. Prüfer K, Racimo F, Patterson N, Jay F, Sankararaman S, Sawyer S, Heinze A, Renaud G, Sudmant P H, de Filippo C, Li H, Mallick S, Dannemann M, Fu Q, Kircher M, Kuhlwilm M, Lachmann M, Meyer M, Ongyerth M, Siebauer M, Theunert C, Tandon A, Moorjani P, Pickrell J, Mullikin J C, Vohr S H, Green R E, Hellmann I, Johnson P L F, Blanche H, et al.: *The complete genome sequence of a Neanderthal from the Altai Mountains. Nature* 2014, 505:43-9.
3. Fu Q, Li H, Moorjani P, Jay F, Slepchenko S M, Bondarev A a., Johnson P L F, Aximu-Petri A, Prüfer K, de Filippo C, Meyer M, Zwyns N, Salazar-Garcia D C, Kuzmin Y V., Keates S G, Kosintsev P a., Razhev D I, Richards M P, Peristov N V., Lachmann M, Douka K, Higham T F G, Slatkin M, Hublin J-J, Reich D, Kelso J, Viola T B, Pääbo S: *Genome sequence of a 45,000-year-old modern human from western Siberia. Nature* 2014:8-13.
4. Green R E, Krause J, Briggs A W, Maricic T, Stenzel U, Kircher M, Patterson N, Li H, Zhai W, Fritz M H-Y, Hansen N F, Durand E Y, Malaspinas A-S, Jensen J D, Marques-Bonet T, Alkan C, Prüfer K, Meyer M, Burbano H a, Good J M, Schultz R, Aximu-Petri A, Butthof A, Höber B, Höffner B, Siegemund M, Weihmann A, Nusbaum C, Lander E S, Russ C, et al.: *A draft sequence of the Neandertal genome. Science* 2010, 328:710-22.
5. Skoglund P, Malmstrom H, Raghavan M, Stora J, Hall P, Willerslev E, Gilbert M T P, Gotherstrom a., Jakobsson M: *Origins and Genetic Legacy of Neolithic Farmers and Hunter-Gatherers in Europe. Science* (80-) 2012, 336: 466-469.
6. Lalueza-Fox C, Gigli E, Bini C, Calafell F, Luiselli D, Pelotti S, Pettener D: *Genetic analysis of the presumptive blood from Louis XVI, King of France. Forensic Sci Int Genet* 2011, 5:459-63.
7. King T E, Fortes G G, Balaresque P, Thomas M G, Balding D, Delser P M, Neumann R, Parson W, Knapp M, Walsh S, Tonasso L, Holt J, Kayser M, Appleby J, Forster P, Ekserdjian D, Hofreiter M, Schürer K: *Identification of the remains of King Richard III*. Nat Commun 2014, 5:5631.
8. Handt O, Krings M, Ward R H, Pääbo S: *The retrieval of ancient human DNA sequences.* Am J Hum Genet 1996, 59:368-376.
9. Pasaniuc B, Rohland N, McLaren P J, Garimella K, Zaitlen N, Li H, Gupta N, Neale B M, Daly M J, Sklar P, Sullivan P F, Bergen S, Moran J L, Hultman C M, Lichtenstein P, Magnusson P, Purcell S M, Haas D W, Liang L, Sunyaev S, Patterson N, de Bakker P I W, Reich D, Price A L: *Extremely low-coverage sequencing and imputation increases power for genome-wide association studies.* Nat Genet 2012, 44:631-635.
10. Gamba C, Jones E R, Teasdale M D, McLaughlin R L, Gonzalez-Fortes G, Mattiangeli V, Domboróczki L, Kövári I, Pap I, Anders A, Whittle A, Dani J, Raczky P, Higham T F G, Hofreiter M, Bradley D G, Pinhasi R: *Genome flux and stasis in a five millennium transect of European prehistory.* Nat Commun 2014, 5:5257.
11. Slatkin M: *Linkage disequilibrium—understanding the evolutionary past and mapping the medical future.* Nat Rev Genet 2008, 9:477-85.
12. Gutenkunst R N, Hernandez R D, Williamson S H, Bustamante C D: *Inferring the joint demographic history of multiple populations from multidimensional SNP frequency data.* PLoS Genet 2009, 5:e1000695.
13. Li H, Durbin R: *Fast and accurate long-read alignment with Burrows-Wheeler transform.* Bioinformatics 2010, 26:589-95.
14. Abecasis G R, Auton A, Brooks L D, DePristo M a, Durbin R M, Handsaker R E, Kang H M, Marth G T, McVean G a: *An integrated map of genetic variation from 1,092 human genomes.* Nature 2012, 491:56-65.
15. Li H, Handsaker B, Wysoker A, Fennell T, Ruan J, Homer N, Marth G, Abecasis G, Durbin R: *The Sequence Alignment/Map format and SAMtools.* Bioinformatics 2009, 25:2078-2079.
16. Hudson R R: Hudson, R. R. (2002) Generating samples under a Wright-Fisher neutral model of genetic variation. Bioinformatics 18: 337-338 (2009).

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein, as needed for the purpose of describing and enabling the method or material referred to.

What is claimed is:

1. A method for determining whether a first human genomic sample and a second human genomic sample are from the same individual, comprising:
    (a) obtaining, by massively parallel sequencing, a plurality of nucleotide sequence reads from a first human genomic sample and a second human genomic sample, wherein the sequencing is performed at a coverage of 0.5% or greater of the genome of the first human genomic sample and the genome of the second human genomic sample, mapping the sequence reads to a chromosome or genome, thereby generating mapped reads, and observing alleles at hundreds of thousands or more polymorphic sites in the mapped reads, thereby determining mapped polymorphisms;
    (b) obtaining linkage disequilibrium (LD) log-likelihood ratios (LLRs) for pairs of the mapped polymorphisms determined in step (a), wherein each pair comprises a polymorphism in the first genomic sample and a polymorphism in the second genomic sample, and wherein the LLRs reflect the likelihood that the mapped polymorphisms determined in step (a) derive from the same individual or different individuals; and
    (c) determining an aggregate likelihood that the first genomic sample and the second genomic sample are from the same individual by summation of LLRs obtained in step (b).

2. The method of claim 1 wherein said aggregate likelihood is determined using LD information from a SNP database.

3. The method of claim 1 wherein SNP linkage information is obtained from a database containing a listing of SNP sequences, genotypes, and locations across a genome.

4. The method of claim 1, wherein the first genomic sample and the second genomic sample are independently selected from the group consisting of: a blood sample, a hair sample, a hair root sample, a saliva sample, a semen sample, a bone marrow sample, and combinations thereof.

5. The method of claim 1, wherein the mapped polymorphisms in step (a) are selected from the group consisting of variable number tandem repeats (VNTRs), simple-tandem repeats, short tandem repeats (STRs), single nucleotide polymorphisms (SNPs), and human mitochondrial DNA (mtDNA) first hypervariable region (HVI) and second hypervariable region (HVII).

6. The method of claim 1, wherein the mapped polymorphisms in step (a) are SNPs.

7. The method of claim 6, wherein said SNPs are recorded in a publicly available archive containing chromosomal locations of SNPs within the archive.

8. The method of claim 6, wherein said SNPs occur in unique subsequences within a genome.

9. The method of claim 6, wherein said SNPs occur in at least one percent of a population.

10. The method of claim 1, wherein the massively parallel sequencing generates read lengths between 50 bp and 350 bp.

11. The method of claim 10, wherein said sequencing comprises a step of randomly fragmenting genomic DNA in a sample.

12. The method of claim 1, wherein the sequencing is performed at a coverage between 1% and 10% of the genome of the first genomic sample and the genome of the second genomic sample.

13. The method of claim 1, wherein obtaining LD LLRs comprises sliding windows of polymorphisms located in proximity on a chromosome.

14. The method of claim 1 wherein said LD LLRs are determined using LD information from a polymorphism database.

15. The method of claim 1, wherein step (a) comprises observing alleles at millions of polymorphic sites in the mapped reads.

16. The method of claim 1, wherein step (b) further comprises comparing the mapped polymorphisms determined in step (a) with a reference set of mapped polymorphisms.

17. The method of claim 16, wherein the reference set of mapped polymorphisms are SNPs.

18. The method of claim 17, wherein the reference set of mapped polymorphisms comprises millions of SNPs.

19. The method of claim 17, wherein the reference set of mapped polymorphisms comprises 90 million SNPs.

* * * * *